us005541202A

United States Patent [19]

Skuballa et al.

[11] Patent Number: 5,541,202
[45] Date of Patent: Jul. 30, 1996

[54] NEW LEUKOTRIENE-B4 ANTAGONISTS AND THEIR USE AS PHARMACEUTICAL AGENTS

[75] Inventors: Werner Skuballa; Bernd Buchmann; Josef Heindl; Wolfgang Fröhlich; Roland Ekerdt; Claudia Giesen, all of Berlin, Germany

[73] Assignee: Schering Aktiengesellschaft, Berlin, Germany

[21] Appl. No.: 193,192
[22] PCT Filed: Aug. 6, 1992
[86] PCT No.: PCT/EP92/01816
§ 371 Date: Jun. 28, 1994
§ 102(e) Date: Jun. 28, 1994
[87] PCT Pub. No.: WO93/04056
PCT Pub. Date: Mar. 4, 1993

[30] Foreign Application Priority Data

Aug. 15, 1991 [DE] Germany ............ 41 27 193.9

[51] Int. Cl.⁶ .................. A61K 31/38; A61K 31/44; C07D 333/32; C07D 409/06
[52] U.S. Cl. ............ 514/336; 514/58; 514/445; 536/103; 549/66; 546/280.4
[58] Field of Search ............ 546/284; 549/66; 514/336, 58, 445; 536/103

[56] References Cited

U.S. PATENT DOCUMENTS

| 4,992,576 | 2/1991 | Gapinski | 560/52 |
| 4,999,436 | 3/1991 | Witzel et al. | 549/45 |
| 5,235,064 | 8/1993 | Gapinski | 548/253 |

FOREIGN PATENT DOCUMENTS

| 0276064 | 7/1988 | European Pat. Off. |
| 0318066 | 5/1989 | European Pat. Off. |
| 9204311 | 3/1992 | WIPO |

OTHER PUBLICATIONS

Nobles et al. Journal of Pharmaceutical Sciences vol. 53 No. 2 1964 pp. 115–126.
Thiophene and Its Derivatives 1952 Interscience Publishers Inc. N.Y. by Blicke. Thornber Chemical Society Reviews vol. 8, No. 4, 1979. pp. 563–580.

Primary Examiner—Jane Fan
Attorney, Agent, or Firm—Millen, White, Zelane, & Braningan, P.C.

[57] ABSTRACT

1. Leukotriene-$B_4$ antagonists of formula I,

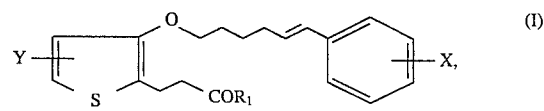

are described,
in which

X represents $C_1$–$C_4$-alkoxy or —S(O)$_p$—($C_1$–$C_4$)-alkyl, p represents 0, 1 or 2

Y represents a hydrogen atom or the radical CO—A—COR$_2$ with A meaning an alkylene group with 1–6 C atoms in the chain or a radical

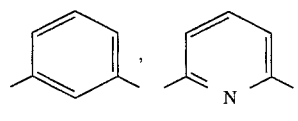

or

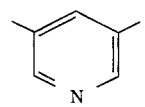

$R_1$ and $R_2$ represents the radical OH, —O—($C_1$–$C_4$)-alkyl, —O—($C_3$–$C_6$)-cycloalkyl, —O—($C_7$–$C_{12}$)-aralkyl or the radical NR$_3$R$_4$ with R$_3$ and R$_4$ meaning hydrogen, ($C_1$–$C_4$)-alkyl, ($C_3$–$C_6$)-cycloalkyl, ($C_6$–$C_{10}$)-aryl or ($C_7$–$C_{12}$)-aralkyl as well as their salts with physiologically compatible bases and their cyclodextrin clathrates, process for their production and their use as pharmaceutical agents.

6 Claims, No Drawings

NEW LEUKOTRIENE-B4 ANTAGONISTS AND THEIR USE AS PHARMACEUTICAL AGENTS

This application is a 371 of PCT/EP92/01816 08/06/92 now WO 93/04056.

The invention relates to new leukotriene-$B_4$ antagonists, process for their production as well as their use as pharmaceutical agents.

Leukotriene $B_4$ ($LTB_4$) was discovered in 1979 by B. Samuelsson et al. as a metabolite of arachidonic acid. In the biosynthesis, leukotriene $A_4$ is formed by the enzyme 5-lipoxygenase first as a central intermediate product, which then is converted by a specific hydrolase to the $LTB_4$.

KEY:

Arachidonsäure=arachidonic acid
Leukotrien $A_4$ ($LTA_4$)=leukotriene $A_4$ ($LTA_4$)
Glutathion - S-transferase=glutathione - S-transferase
Leukotrien $B_4$ ($LTB_4$)=leukotriene $B_4$ ($LTB_4$)
Leukotrien $C_4$ ($LTC_4$)=leukotriene $C_4$ ($LTC_4$)

recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson et al., Science 237, 1171 (1987). d) C. W. Parker, Drug Development Research 10, 277 (1987). It follows from the above that $LTB_4$ is an important inflammation mediator for inflammatory diseases, in which leukocytes invade the affected tissue.

It is known from the $LTB_4$ that it causes the adhesion of leukocytes to the blood vessel wall. $LTB_4$ is chemotactically effective, i.e., it triggers a directed migration of leukocytes in the direction of a gradient of increasing concentration. Further, because of its chemotactic activity, it indirectly changes the vascular permeability, and a synergism with prostaglandin $E_2$ is observed. $LTB_4$ obviously plays a decisive role in inflammatory, allergic and immunological processes.

Leukotrienes and especially $LTB_4$ are involved in skin diseases, which accompany inflammatory processes (increased vessel permeability and formation of edemas, cell infiltration), increased proliferation of skin cells and itching, such as, for example, in eczemas, erythemas, psoriasis,

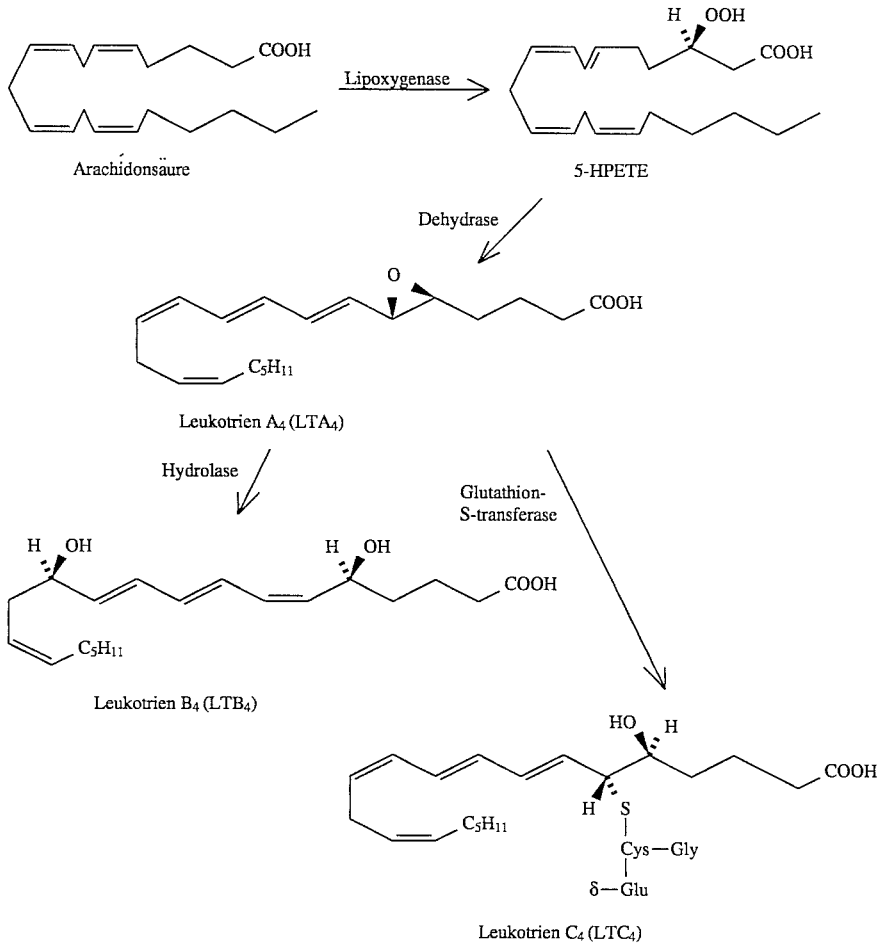

The nomenclature of the leukotrienes can be gathered from the following works:

a) B. Samuelsson et al., Prostaglandins 19, 645 (1980); 17, 785 (1979).

b) C. N. Serhan et al., Prostaglandins 34, 201 (1987).

The physiological and especially the pathophysiological importance of leukotriene $B_4$ is summarized in several more pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis or atopic dermatitis.

Further, leukotrienes and $LTB_4$ are involved especially in arthritis, chronic lung diseases (e.g., asthma), rhinitis and inflammatory intestinal diseases.

Antagonists to $LTB_4$ itself or inhibitors of those enzymes which are involved in the synthesis of the $LTB_4$ can be effective as specific medications, especially against diseases which accompany inflammations and allergic reactions.

Compounds with a carboxybenzenephenylpropionic acid structure that have leukotriene-$D_4$ and leukotriene-$B_4$ antagonistic properties are already known from EP276064.

Compounds were found that surprisingly strongly antagonize the effect of the natural $LTB_4$.

The invention relates to leukotriene-$B_4$ antagonists of formula I,

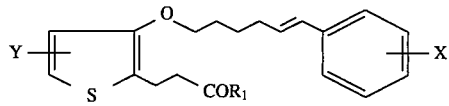 (I)

in which

X represents $C_1$–$C_4$-alkoxy or —$S(O)_p$—($C_1$–$C_4$)-alkyl, p represents 0, 1 or 2

Y represents a hydrogen atom or the radical CO—A—COR with A meaning an alkylene group with 1–6 C atoms in the chain or a radical

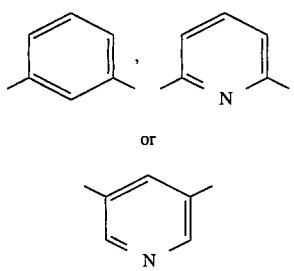

or $R_1$ and $R_2$ represent the radical OH,
—O—($C_1$–$C_4$)-alkyl, —O—($C_3$–$C_6$)-cycloalkyl, —O—($C_6$–$C_{10}$)-aryl, —O—($C_7$–$C_{12}$)-aralkyl or the radical $NR_3R_4$ with $R_3$ meaning hydrogen, ($C_1$–$C_4$)-alkyl, ($C_3$–$C_6$)-cycloalkyl or ($C_7$–$C_{12}$)-aralkyl and $R_4$ meaning ($C_1$–$C_4$)-alkyl, ($C_3$–$C_6$)-cycloalkyl or ($C_7$–$C_{12}$)-aralkyl as well as their salts with physiologically compatible bases and their cyclodextrin clathrates.

X, $R_1$ and $R_2$ as $C_1$–$C_4$-alkoxy group can mean: methoxy, ethoxy, n-propoxy, isopropxy, n-butoxy, sec.-butoxy and tert.-butoxy.

The $C_1$–$C_4$-alkyl radical in the group —$S(O)_p$—($C_1$–$C_4$)-alkyl of X as radical $R_3$ or as radical $R_4$ can be: methyl, ethyl, n-propylisopropyl, n-butyl, sec.-butyl, tert.-butyl.

As alkylene group Y with 1–6 C atoms straight-chain or branched-chain, saturated radicals are suitable such as, e.g., methylene, ethylene, trimethylene, tetramethylene, hexamethylene, 1-methyltrimethylene, 1-methyl-tetramethylene, 1,1-dimethyltrimethylene, etc.

The radical ($C_3$–$C_6$)-cycloalkyl (for $R_1$, $R_2$, $R_3$ and $R_4$) can be: cyclopropyl, cyclobutyl, cyclopentyl or cyclohexyl.

As radicals $C_6$–$C_{10}$-aryl in the definition of $R_1$ and $R_2$, phenyl, 1-naphthyl, 2-naphthyl are suitable.

Finally, the radicals $C_7$–$C_{12}$-aralkyl in the definitions of $R_1$, $R_2$, $R_3$ and $R_4$ represent the following groups: benzyl, phenethyl, 3-phenylpropyl, 4-phenylbutyl, 1-methyl-3-phenylpropyl, 1-methyl-2-phenyl-ethyl, etc.

Inorganic and organic bases are suitable for salt formation, as they are known to one skilled in the art for forming physiologically compatible salts. For example, there can be mentioned alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

To achieve the cyclodextrin clathrates, the compounds of formula I with α, β or γ-cyclodextrin are reacted. The β-cyclodextrin clathrates are preferred.

The invention further relates to a process for the production of leukotriene-$B_4$ antagonists of formula I characterized in that in a way known in the art a compound of formula II

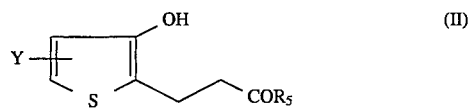 (II)

in which Y has the above-indicated meaning and $R_5$ means the radical OH or CO—$CH_2$—$COOR_6$, in which $R_6$ represents a $C_1$–$C_4$-alkyl group, is reacted with a compound of formula III

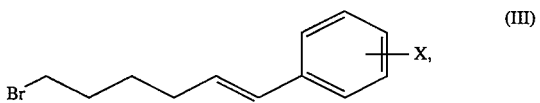 (III)

in which X has the above-indicated meaning, in the presence of cesium, lithium or potassium carbonate and optionally saponifies the ester groups, esterifies carboxyl groups or the obtained acids of formula I with organic and inorganic bases or cyclodextrins.

The above-mentioned process (II+III=>1) is performed in organic solvents, such as, e.g., dimethylformamide, at temperatures between 0° and 100° C., preferably at temperatures between 20° and 60° C. with stirring in the course of 5–24 hours in the presence of cesium, lithium or potassium carbonate.

The reduction of carbonyl group A takes place preferably with sodium borohydride under usual conditions. The obtained hydroxymethylene compounds optionally can be separated in the optic antipodes.

The production of the compounds of formulas II and III necessary for this reaction takes place according to the processes indicated in the examples or those indicated in the reference examples.

The saponification of the esters of formula I is performed according to methods known to one skilled in the art, such as, for example, with basic catalysts.

The introduction of the ester group

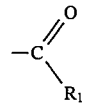

in which $R_1$ represents an O-alkyl group with 1–4 C atoms, takes place according to the methods known to one skilled in the art. The 1-carboxy compounds are reacted, for example, with diazohydrocarbons in a way known in the art. The esterification with diazohydrocarbons takes place, e.g., in that a solution of the diazohydrocarbon in an inert solvent, preferably in diethyl ether, is mixed with the 1-carboxy compound in the same or in another inert solvent, such as, e.g., methylene chloride. After completion of the reaction in 1 to 30 minutes, the solvent is removed and the ester is purified in the usual way. Diazoalkanes are either known or can be produced according to known methods [Org. Reactions Vol. 8, pages 389–394 (1954)].

The introduction of ester group

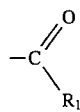

in which R¹ represents an O-aryl group takes place according to the methods known to one skilled in the art. For example, the 1-carboxy compounds with the corresponding arylhydroxy compounds are reacted with dicyclohexylcarbodiimide in the presence of a suitable base, for example, pyridine, DMAP, triethylamine, in an inert solvent. As solvent, methylene chloride, ethylene chloride, chloroform, ethyl acetate, tetrahydrofuran, preferably chloroform, are suitable. The reaction is performed at temperatures between −30° C. and +50° C., preferably at 10° C.

The leukotriene-$B_4$ antagonists of formula I with $R^1$ meaning a COOH group can be converted to a salt with suitable amounts of the corresponding inorganic bases with neutralization. For example, during dissolving of the corresponding acids in water, which contains the stoichiometric amount of the base, the solid inorganic salt is obtained after evaporation of the water or after addition of a water-miscible solvent, e.g., alcohol or acetone.

For the production of an amine salt, the $LTB_4$ acid, e.g., is dissolved in a suitable solvent, for example, ethanol, acetone, diethyl ether, acetonitrile or benzene and at least the stoichiometric amount of the amine is added to this solution. In this way, the salt usually accumulates in solid form or is isolated after evaporation of the solvent in the usual way.

The introduction of amide group

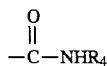

takes place according to the methods known to one skilled in the art. The carboxylic acids of formula I ($R_1$=OH) are first converted to the mixed anhydride in the presence of a tertiary amine, such as, for example, triethylamine, with chloroformic acid isobutyl ester. The reaction of the mixed anhydride with the alkali salt of the corresponding amine or with ammonia takes place in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C.

The compounds of formula II being used as initial material can be produced in a way known in the art, for example, by 3-oxy-2-carbomethoxy-thiophene (N. Fiesselmann et. al., Chemische Berichte 87, 841 (1954)) being silylated with tert.-butyldimethylsilyl chloride and by subsequent reduction with diisobutyl aluminum hydride being converted into the primary alcohol of formula IV.

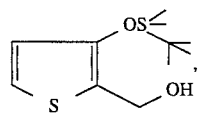

Oxidation of the primary hydroxy group in IV with manganese dioxide to the corresponding aldehyde and Wittig Horner olefination with phosphonoacetic acid trialkyl ester as well as subsequent silyl ether cleavage with tetrabutylammonium fluoride, benzoylation and hydrogenation of the α, β-unsaturated ester yields the benzoate of formula V

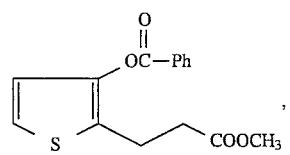

Friedel Crafts acylation of V and subsequent benzoate saponification led to the alcohol of general formula II.

The compounds of formula I act in an antiinflammatory and antiallergic manner. Consequently the new leukotriene-$B_4$ derivatives of formula I represent valuable pharmaceutical active ingredients. The compounds of formula I are especially suitable for topical administration, since they exhibit a dissociation between desired topical effectiveness and undesirable systemic side effects.

The new leukotriene-$B_4$ antagonists of formula I are suitable in combination with the auxiliary agents and vehicles usual in galenic pharmaceutics for topical treatment of contact dermatitis, eczemas of the most varied types, neurodermatoses, erythrodermia, pruritus vulvae et ani, rosacea, lupus erythematosus cutaneus, psoriasis, lichen ruber planus et verrucosis and similar skin diseases.

The production of the pharmaceutical agent specialties takes place in the usual way by the active ingredients being converted with suitable additives to the desired form of administration, such as, for example: solutions, lotions, ointments, creams or plasters.

In the thus formulated pharmaceutical agents, the active ingredient concentration depends on the form of administration. In lotions and ointments, an active ingredient concentration of 0.0001% to 1% is preferably used.

Further, the new compounds optionally in combination with the usual auxiliary agents and vehicles are also well-suited for the production of inhalants, which can be used to treat allergic diseases of the respiratory system, such as, for example, bronchial asthma or rhinitis.

Further, the new leukotriene-$B_4$ antagonists are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat allergic diseases of the intestinal tract, such as colitis ulcerosa and colitis granulomatosa.

The new leukotriene-$B_4$ derivatives can also be used in combination, such as, e.g., with lipoxygenase inhibitors, cyclooxygenase inhibitors, prostacyclin agonists, prostaglandin agonists, thromboxane antagonists, leukotriene-$D_4$ antagonists, leukotriene-$E_4$ antagonists, leukotriene-$F_4$ antagonists, phosphodiesterase inhibitors, calcium antagonists or PAF antagonists.

The following embodiments are used to explain the process according to the invention in more detail.

EXAMPLE 1

3-{5-(3-Methoxycarbonylbenzoyl)-3-[6-(4-methoxyphenyl)-(5E)-5-hexenyloxy]-2-thienyl}-propionic acid methyl ester 804 mg of cesium carbonate is added to a solution of 430 mg of 3-[5-(3-Methoxycarbonylbenzoyl)-3-hydroxy-2-thienyl]-propionic acid methyl ester and 332 mg of (1E)-6-bromo-1-(4-methoxyphenyl)-1-hexene in 2.9 ml of dimethylformamide and the suspension is stirred for 21 hours at room temperature. The reaction mixture is filtered, the filtrate residue is washed with dichloromethane, the filtrate is concentrated by evaporation and the residue is chromatographed on silica gel with hexane. 542 mg of the title compound is obtained as colorless oil.

IR(CHCl$_3$): 2942, 1723, 1670, 1628, 1605, 1435, 1375, 995, 993 cm$^{-1}$.

The initial material for the above title compound is produced as follows:

1a)

2-Hydroxymethyl-3-(tert.-butyl-dimethylsilyloxy)-thiophene 4 g of tert.-butyldimethylsilyl chloride and 3.6 g of imidazole are added at 0° C. to a solution of 3 g of 3-oxy-2-carbomethoxy-thiophene (H. Fiesselman et al., Chemische Berichte 87, 841 (1954)) in 15 ml of dimethylformamide and stirred for 22 hours at 22° C. under argon. Then, it is diluted with 500 ml of ether, shaken with 30 ml of 10% sulfuric acid and washed neutral with water. It is dried on magnesium sulfate, concentrated by evaporation in a vacuum and the residue is chromatographed on silica gel. 5.4 g of 2-carbomethoxy-3-(tert.-butyl-dimethylsilyloxy)-thiophene is eluted with hexane/ether (92+8) as colorless oil.

For reduction of the ester group, 1.1 g of the above-produced silyl ether is dissolved in 25 ml of toluene and 6.7 ml of a 1.2 molar solution of diisobutyl aluminum hydride in toluene is instilled at −70° C. It is stirred for 25 minutes at −70° C., mixed with 2 ml of isopropanol, stirred for 3 minutes, 3.3 ml of water is added, stirred for 2 hours at 22° C. mixed with ethyl acetate, filtered and concentrated by evaporation in a vacuum. In this way, 1.1 g of the title compound is obtained as colorless oil.

IR: 3600, 3450, 2960, 2935, 2860, 1605, 1555, 1395, 840, 826 cm$^{-1}$.

1b)

3-((3-Benzoyloxy)-2-thienyl)-propionic acid-methyl ester 1.8 g of manganese dioxide is added within 20 minutes to a solution of 490 mg of the alcohol, produced according to example 1a, in 3 ml of toluene and stirred for 2.5 hours at 22° C. Then it is filtered, concentrated by evaporation in a vacuum and the residue is chromatographed on silica gel. 390 mg of the aldehyde is obtained as colorless oil with hexane/ether (9+1).

IR: 2960, 2938, 1650, 1530, 1435, 1410, 830 cm$^{-1}$.

For olefination reaction, a solution of 352 mg of phosphonoacetic acid trimethyl ester in 3.7 ml of tetrahydrofuran is instilled at 0° C. in a suspension of 78 mg of sodium hydride (55% in mineral oil) in 6.8 ml of tetrahydrofuran, 76 mg of anhydrous lithium chloride is added and stirred for 10 minutes at 0° C. Then a solution of 360 mg of the above-produced aldehyde in 2.2 ml of tetrahydrofuran is instilled, stirred for 3 hours at 0° C. and then neutralized with acetic acid. It is diluted with ether, washed twice with water, dried on sodium sulfate and concentrated by evaporation in a vacuum. The residue is purified by chromatography.

8.8 g of the above-produced benzoate is dissolved in 80 ml of ethyl acetate, 900 mg of palladium (10% on carbon) is added and hydrogenated in an autoclave for 3 hours at 22° C. and 10 bars pressure. Then it is filtered and concentrated by evaporation. The residue is purified by chromatography on silica gel. 6.65 g of the title compound is obtained with hexane/ether (7+3) as pale yellow colored oil.

IR: 2958, 1736, 1625, 1604, 1263 cm$^{-1}$.

1c)

3-{5-(Methoxycarbonylbenzoyl)-3-hydroxy-2-thienyl}-propionic acid methyl ester 5.5 ml of a solution of aluminum chloride in nitromethane (production: 10 g of aluminum chloride is dissolved in 10 ml of nitromethane) is instilled to a solution of 4 g of the benzoate produced in example 1b and 4.1 g of isophthalic acid monomethyl ester chloride in 4.9 ml of nitromethane and stirred for 20 minutes at 0° C. and 2 hours at 22° C. Then it is poured on 50 ml of ice water, shaken three times with ether, the organic phase is washed with sodium bicarbonate solution and water, dried on sodium sulfate and concentrated by evaporation in a vacuum. The residue is purified by chromatography on silica gel. In this way, 1.8 g of the ketone is obtained as colorless oil with ether/hexane (1+1).

IR: 2960, 1736, 1640, 1602, 1260 cm$^{-1}$.

For benzoate cleavage, 168 mg of anhydrous potassium carbonate is added to a solution of 1.1 g of the above-produced ketone in 22 ml of methanol and stirred for 2.5 hours at 22° C. under argon. Then it is acidified with 5% sulfuric acid, diluted with water, washed neutral with brine, dried on magnesium sulfate and concentrated by evaporation in a vacuum. The residue is chromatographed on silica gel. In this way, 0.7 g of the title compound is obtained as yellowish oil with ether/hexane (1+1).

IR (KBr): 3420 (broad), 3180, 2960, 1740, 1725, 1610 cm$^{-1}$.

EXAMPLE 2

3-{5-(3-Carboxybenzoyl)-3-[6-(4-methoxyphenyl)-(5E)-5-hexenylgxy]-2-thienyl}-propionic acid 3.1 ml of an anhydrous 1 normal potassium hydroxide solution is added to a solution of 415 mg of the diester, produced in example 1, in 3.1 ml of methanol and stirred for 4 hours at 22° C. Then it is acidified with 10% sulfuric acid to pH 2, extracted with ethyl acetate, the organic phase is washed with brine, dried with sodium sulfate and concentrated by evaporation in a vacuum. The residue is purified by chromatography on silica gel. 274 mg of the title compound is obtained as colorless crystals with ethyl acetate/hexane (melting point 133° C. recrystallized from ethyl acetate/hexane).

IR (KBr): 3420, 2955, 1700, 1638, 1605, 1510 cm$^{-1}$.

We claim:

1. A leukotriene-B$_4$ antagonist of formula I

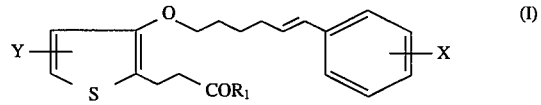

wherein

X is C$_1$–C$_4$-alkoxy or —S(O)$_p$—(C$_1$–C$_4$)-alkyl, p is 0, 1 or 2

Y is a hydrogen atom or the radical CO—A—COR$_2$, wherein A is a C$_{1-6}$-alkylene group, or a radical

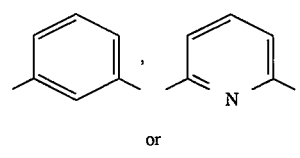

or

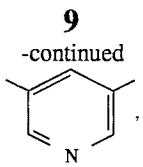

$R_1$ and $R_2$ are each independently the radical OH, —O—$(C_1$–$C_4)$-alkyl, —O—$(C_3$–$C_6)$-cycloalkyl, —O—$(C_6$–$C_{10})$-aryl, —O—$(C_7$–$C_{12})$-aralkyl, or the radical $NR_3R_4$ wherein $R_3$ and $R_4$ are each independently hydrogen, $(C_1$–$C_4)$-alkyl, $(C_3$–$C_6)$-cycloalkyl or $(C_7$–$C_{12})$-aralkyl, or a salt thereof with a physiologically compatible base, or a cyclodextrin clathrate thereof.

2. A compound of claim 1, which is

3-{5-(3-methoxycarbonylbenzoyl)-3-[6 -(4-methoxyphenyl)-(5E)-5-hexenyloxy]-2-thienyl}-propionic acid methyl ester, or 3-{5-(3-carboxybenzoyl)-3-[6-(4-methoxyphenyl)-(5E )-5-hexenyloxy]- 2-thienyl}-propionic acid.

3. A pharmaceutical composition comprising an effective amount of a compound of claim 1 and a pharmaceutically acceptable auxiliary agent or vehicle.

4. A pharmaceutical composition comprising an effective amount of a compound of claim 2 and a pharmaceutically acceptable auxiliary agent or vehicle.

5. A pharmaceutical composition of claim 3 which is administered topically.

6. A pharmaceutical composition of claim 4 which is administered topically.

* * * * *